United States Patent [19]

Steele et al.

[11] Patent Number: 5,184,893
[45] Date of Patent: Feb. 9, 1993

[54] AUTOMATIC CAPSULE MIXING DEVICE

[75] Inventors: Charles E. Steele; Mark R. Anderson, both of Canton; James C. Hamilton, Ann Arbor, all of Mich.

[73] Assignee: Kerr Manufacturing Company, Romulus, Mich.

[21] Appl. No.: 691,489

[22] Filed: Mar. 25, 1991

[51] Int. Cl.⁵ ............................................. B01F 11/00
[52] U.S. Cl. .................................. 366/209; 366/208; 366/601; 366/602
[58] Field of Search .................... 366/208–210, 366/215, 216, 218, 219, 601, 602, 53; 235/493

[56] References Cited

U.S. PATENT DOCUMENTS

| | | | |
|---|---|---|---|
| 2,458,692 | 1/1949 | Downer | 366/602 |
| 3,198,502 | 8/1965 | Thompson | 366/602 |
| 3,749,371 | 7/1973 | Folkenroth et al. | 366/602 |
| 3,949,501 | 4/1976 | Andrews et al. | 235/493 |
| 4,184,776 | 1/1980 | Shampanier | 366/602 |
| 4,371,259 | 2/1983 | Howitt | 355/38 |
| 4,531,839 | 7/1985 | Cunisse | 366/602 |
| 4,673,297 | 6/1987 | Siczek et al. | 366/208 |
| 4,822,172 | 4/1989 | Stottmann | 366/601 |
| 4,890,931 | 1/1990 | Herold | 366/602 |
| 4,897,533 | 1/1990 | Lyszczarz | 235/493 |

Primary Examiner—Philip R. Coe
Assistant Examiner—James F. Hook
Attorney, Agent, or Firm—Cumpston & Shaw

[57] ABSTRACT

A capsule mixing device which comprises a motor suitable for powering a vibrating mixing arm with vibrating device connected to the motor having at one end thereof an arm for holding a capsule in place during mixing, and card actuator suitable for activating and controlling the motor at a predetermined speed for a predetermined length of time whereby materials contained within the capsule are mixed to a predetermined desired state by action of the vibrating device on the arm.

13 Claims, 10 Drawing Sheets

AUTOMATIC CAPSULE MIXING DEVICE

BACKGROUND OF THE INVENTION

The present invention relates to an automatically controlled capsule mixing device, and more specifically to a device having utility for mixing the contents of dental capsules.

In the dental field, mixing devices for dental materials such as for example, amalgamators, have generally been produced with mechanical rather than microprocessor controls. Therefore, key parameters such as mixing speeds and times are subject to variation and change from batch to batch and material to material, causing the operators to change mixing times and/or speeds. Often, the result is a setting outside the prescribed amount and a mix or a resultant product that does not have the described or optimum handling properties. U.S. Pat. No. 3,198,502 illustrates a device of this type in which the mixing time and speed are controlled by varying control elements on a machine manually under the control and direction of the operator.

U.S. Pat. No. 4,531,839, which is incorporated herein by reference, is directed to an automatic dispenser mixer having utility for mixing and forming a dental amalgam using a predetermined program and electronic control unit in which the key elements comprising the silver powder and mercury are tapped and selectively metered from respective reservoirs with the system in process controlled by the actuation of the conveyors for the material and the mixer through a display and the entry of various parameters to form the desired mixture.

The present invention is directed to improvement over the mechanically controlled mixers and amalgamators such as those illustrated by the 3,198,502 patent and to provide an automatically controlled unit which mixes capsules having a predetermined amount of dental material in order to provide constant performance which enhances the overall quality and use of the product contained therein.

The present invention is directed to a card coded dental mixing device whereby magnetic strip coded cards automatically feed product information to a dental mixing device which automatically mixes the contents of a dental capsule accurately to the desired time and speed necessary to provide products having consistent quality from batch to batch.

SUMMARY OF THE INVENTION

In accordance with the present invention a card coded mixer for capsules containing dental materials is provided which is controlled by a code system which automatically feeds product information to the mixing device. The code may be incorporated in a magnetic or optical track or strip on a card, in the form of perforations in a card or strip, and the like.

In a preferred embodiment the mixing device comprises an amalgamator which is used for mixing powdered metal and mercury in a unit dosage capsule that is instructed for mixing time and speed by a magnetically coded plastic card system. The plastic card system creates a visual display to the operator of product, mixing time, and mixing speed for immediate review prior to activating the unit by pressing a "Start" key. A self-activation system is encompassed into a mixing arm of the device which contains holder for a unit dosage capsule activation of a dental capsule of other similarly activated capsule containing a dental material which requires mixing. The automatic programming feature and automatic activation features of the device allow the operator to carefully control the final product automatically and consistently with minimal effort.

The present invention overcomes previous prior art problems associated with changing mixing speeds and/or times on mixing devices when various sizes (by weight) of unit dosage capsules are used. The present system automatically accommodates each mixing condition upon insertion of the pre-programmed card for brand, time, and speed of mixer.

DETAILED DESCRIPTION OF THE INVENTION

Figure 1:
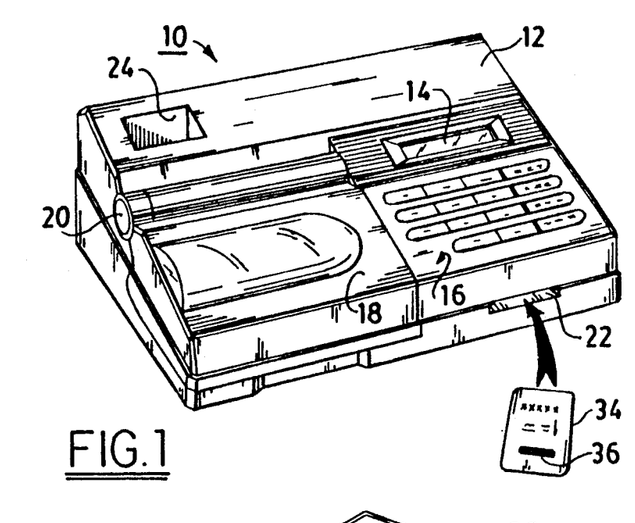
FIG. 1 is a perspective view showing the external housing of the automatic mixing device of the present invention.
Figure 2:
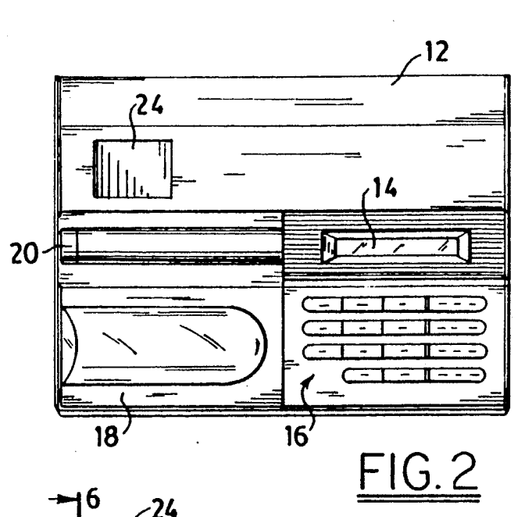
FIG. 2 illustrates a top view of the device of FIG. 1.
Figure 3:
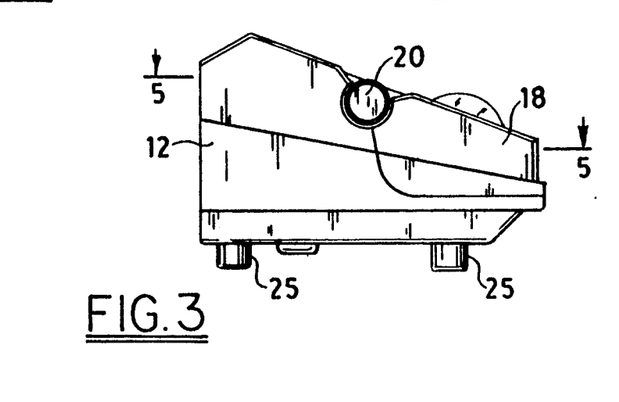
FIG. 3 is a side view of the left side of the device of FIG. 1.
Figure 4:
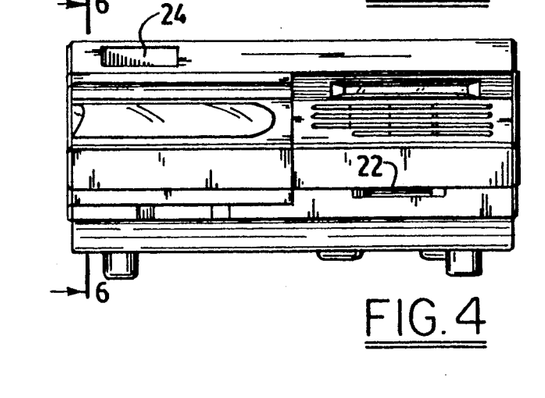
FIG. 4 is a front view of the device of FIG. 1.

As shown in FIG. 1, the capsule mixer 10 is provided with a housing 12 having an LCD display 14, a control panel 16, a safety door 18, a card entry slot 22, and a card storage pocket 24. Door 18, which is hinged at 20 to allow for loading a dental capsule into the interior of the capsule mixer, wherein are contained the capsule agitating or shaking mechanism (not shown in FIG. 1), a card reading magnetic pick-up head 26 (shown in FIG. 6), an electrical control unit 28 (see FIGS. 5 and 22), and various other electrical and non-electrical structures (not shown in FIG. 1) of an ancillary character (e.g., the power supply circuitry). The mixer 10 may be supported on legs 25 located at each of the four bottom corners of the device.

The control panel 16 comprises a small key board (see FIG. 17), preferably of the membrane switch type having sixteen switches, one each for the numerals 0-9, a decimal point, and one each for raising or lowering time setting, and/or speed setting, and starting. Inasmuch as the legendry of FIG. 17 adequately identifies these switches, individual switches with distinct reference numerals have not been provided.

The control panel switches are connected to the control unit 28, essentially a microprocessor-based controller (see FIGS. 5 and 22), for setting into the control unit the time and speed at which it is desired to agitate a dental capsule. Thus, in manual operation, one may press the SET SPEED switch, or the SET TIME switch. The 0-9 and decimal point switches are then used to set in the time or speed of mixing cycle, after which one may press START, in order to cause the capsule mixer to agitate the capsule. In effect, these settings program the control unit to control the motor 32 (see FIGS. 5 and 6) of the capsule mixer mechanism (later to be described in detail) such as to shake the capsule through an off axis camming arrangement connecting the motor to an amalgamator mixing arm assembly for the length of time and at the speed set in by the control panel switches. This mode of agitation is more or less consistent with prior art, as, for instance, the "dispenser mixer" of U.S. Pat. No. 4,531,839.

However, it is contemplated that the capsule mixer will likely be used with a standardized set of capsules. That is, to say the capsules will be furnished in sets in each of which each capsule has the same quantity of amalgam ingredients as each of its fellows, and so requires shaking for the same length of time, and at the same speed. Except as hereafter indicated, the present invention obviates manual setting of speed and time.

Figure 20:
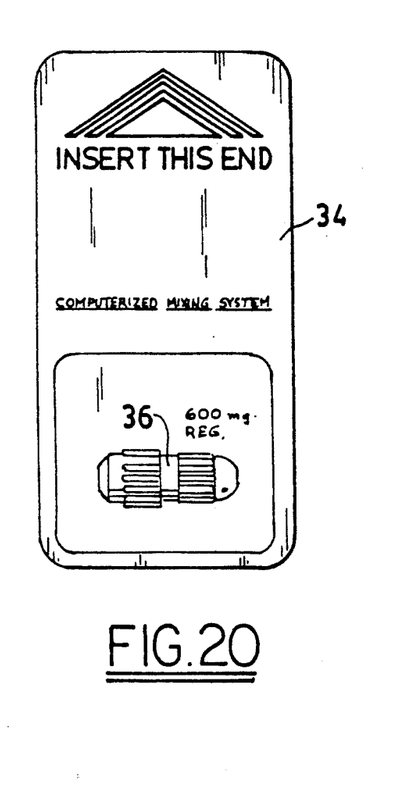
FIG. 20 is a front view of one embodiment of a magnetic card suitable for use with the present invention.
Figure 21:
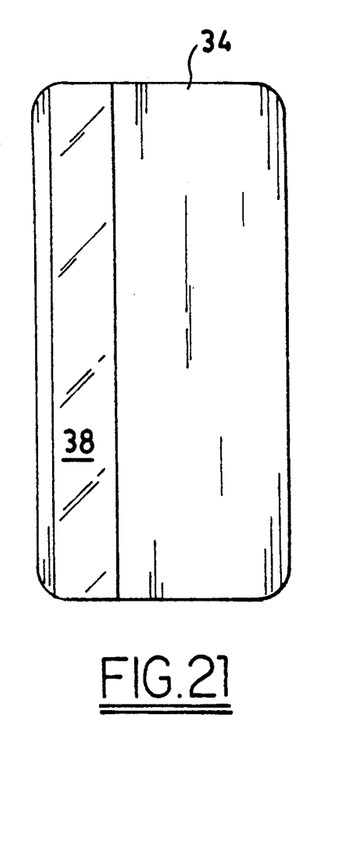
FIG. 21 is a back view of the card illustrated in FIG. 20.

According to the present invention, there is provided a capsule mixer with a set of magnetic cards 34 (only one is shown), normally kept in card storage pocket 24 of housing 12. Each card 34 is visibly coded in such manner as to identify a particular set of capsules, and is also magnetically coded with the same time and speed parameters that the capsules in that particular set require for proper mixing. Thus, in FIGS. 1 and 5, such a magnetic card 34 is shown as bearing thereon a visible icon 36 which illustrates a standard capsule marked, as by color coding, to identify what capsule set the card is to be used with. As shown in FIG. 20, the card may be provided with other visible indicia such as the direction INSERT THIS END, a description of the capsule parameters (e.g., as shown, "600 mg. REG"), and so forth.

Figure 5:
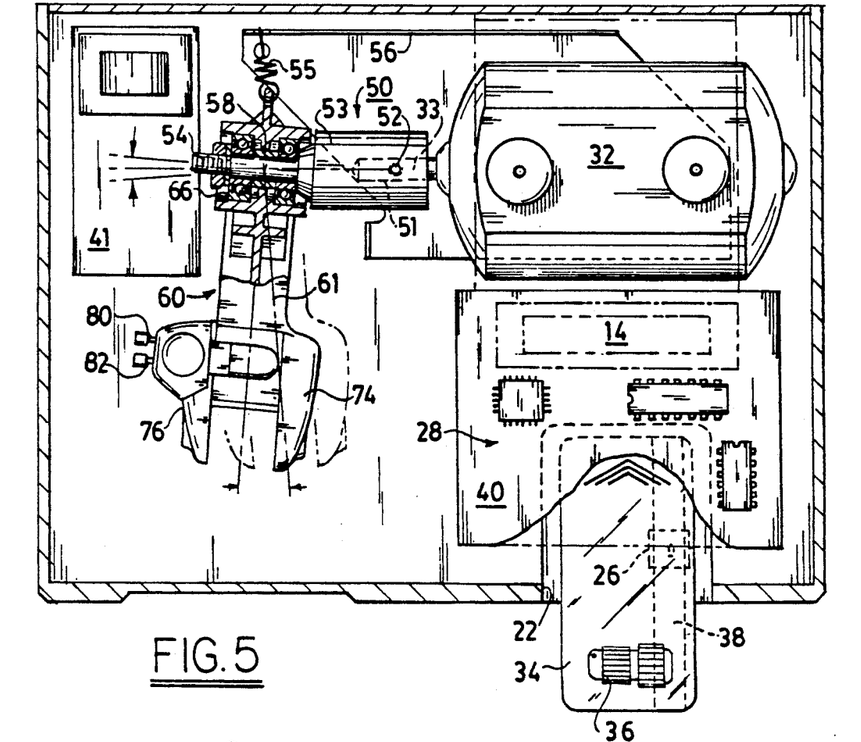
FIG. 5 is an enlarged top view of the device of FIG. 1 with the shell of the outer housing removed.
Figure 6:
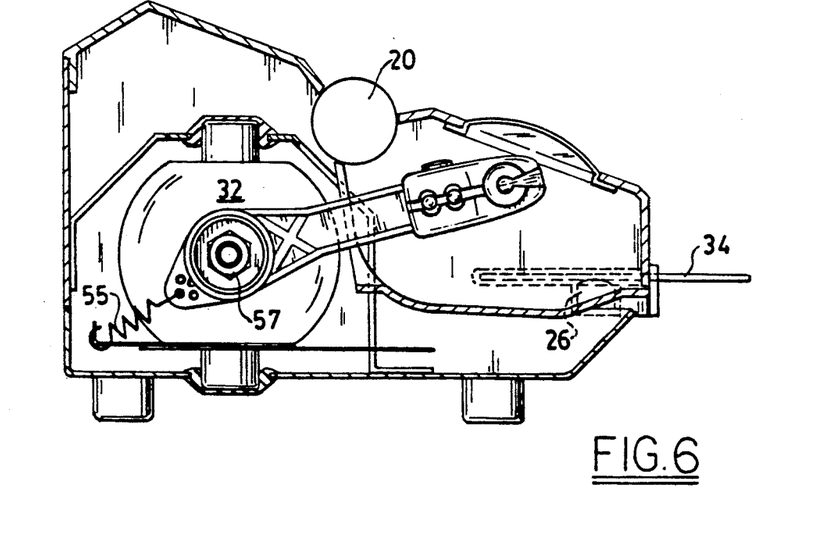
FIG. 6 is a side view of the device of FIG. 5 with the side panel removed.

In FIG. 5 there is shown, in broken lines, a coded track 38 along the length of the obverse side of the card and in the direction of insertion of the card. Card 34 also has coded thereon product name, speed set, and spill size. The coded track 38 encodes the time and speed for the particular capsule in conventional fashion for reading by a conventional pick-up head 26, which will emit a stream of electrical pulses if the track 38 is moved at a moderate, relatively uniform velocity past the pick-up head. These pulses are fed to the control unit 28 and program it, with time and speed, more or less as if one had manually entered that time and speed via the control panel 16.

Figures 17, 18:
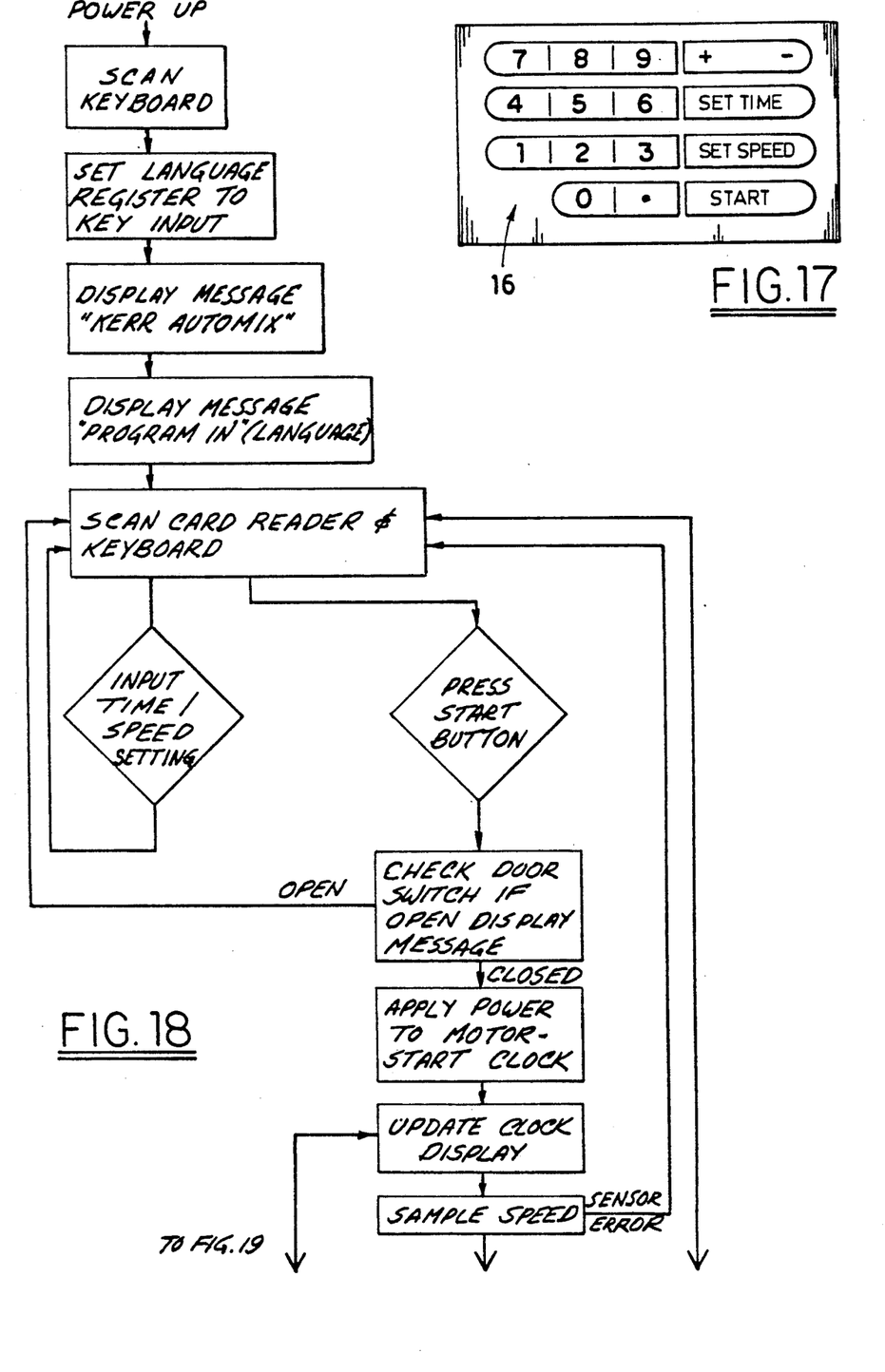
FIG. 17 is an enlarged view illustrating the control panel of the device of the invention.
FIG. 18 is a flow chart illustrating the operation of the device.
Figure 19:
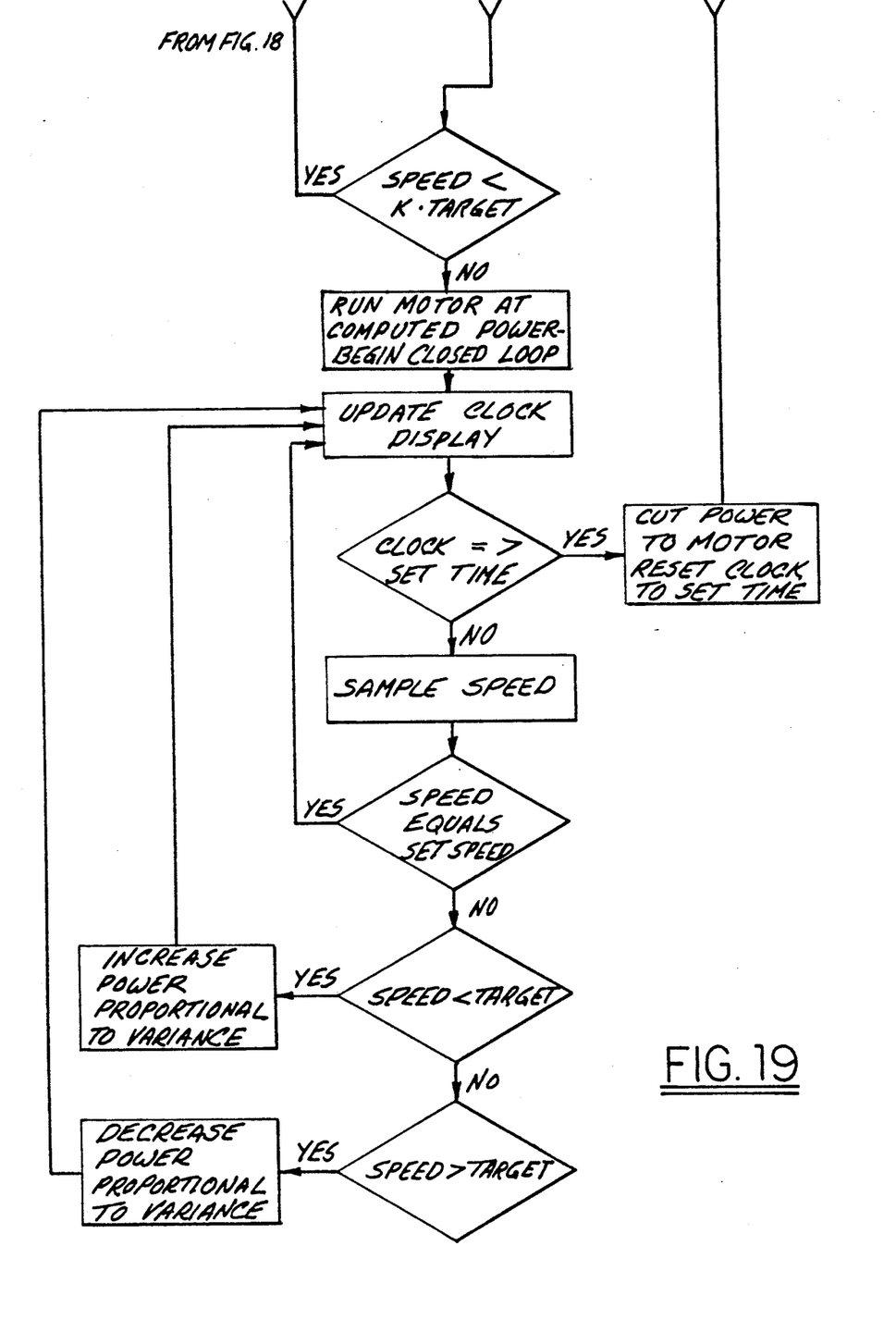
FIG. 19 is a continuation flow diagram of FIG. 18 further illustrating the operation of the device.
Figure 22:
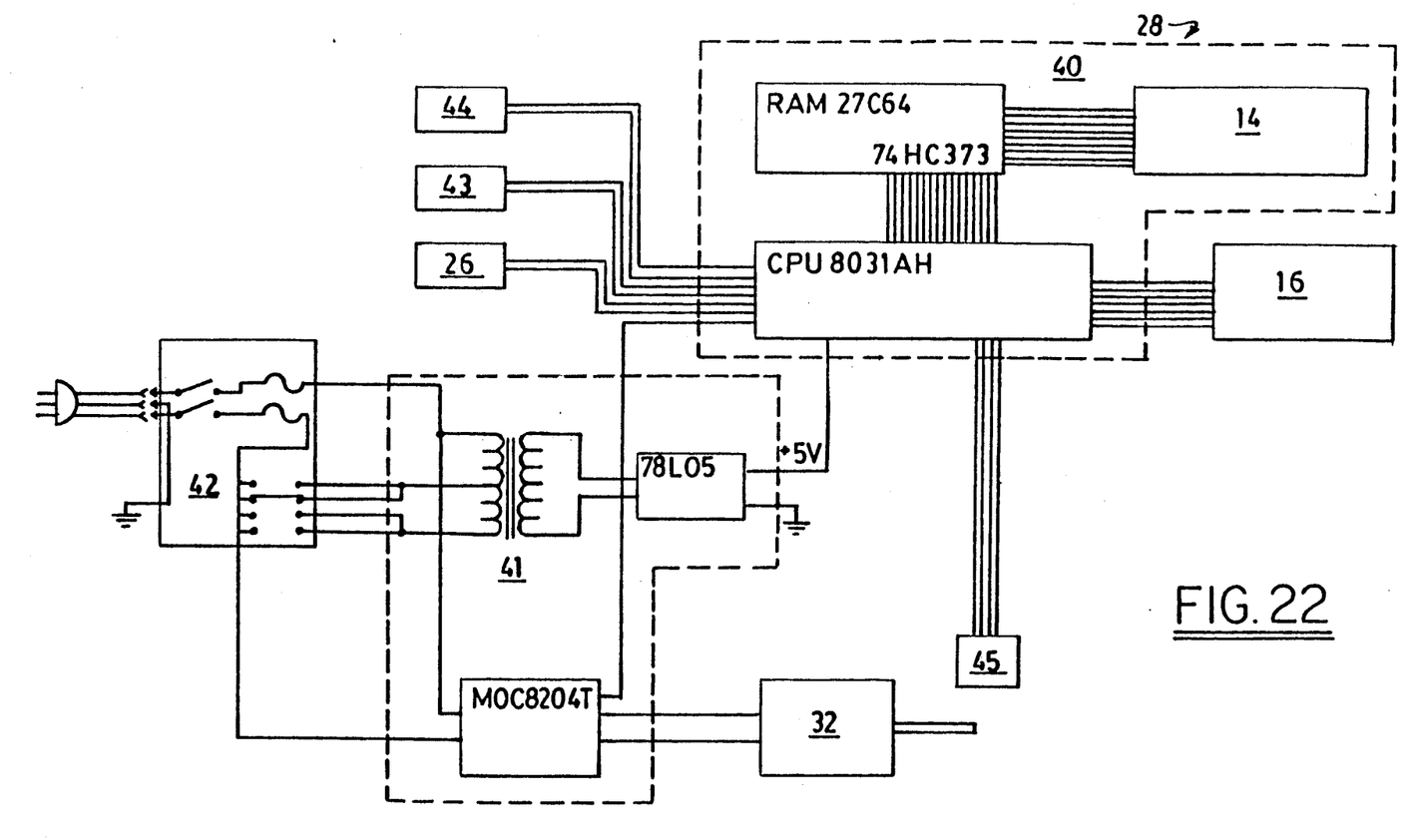
FIG. 22 is a box diagram of the electrical system for operating the automatic mixing device of the present invention.

I believe that only ordinary skill in the art is required in order to provide control means for controlling of agitation speed and time by magnetically coded card and/or keyboard, in accordance with the flow diagrams of FIGS. 18 and 19, and the keyboard of FIG. 17. In the present instance, however, the electrical system for operating the mixing device of the present invention is preferably as shown in FIG. 22. Thus, a board 40, has chips 8031AH, RAM27C64 and 74HC373 thereon representing such control means. Chip 8031AH is a CPU, and functions as a master processor. Chip RAM27C64, which is programmable, functions as firmware storage. Chip 74HC373 is a chip for interfacing the CPU and display 14, and is actually a separate chip. For convenience in illustrating, however, it is shown in the same box as RAM27C64.

Chip MOC8204T is an optical coupler for controlling the motor 32 with rectified mains voltage from rectifying means (not shown) on board 41. The motor 32 is driven by the FET output, which is controlled by signal from chip MOC8204T on power supply board 41, for a time controlled by chip 8031AH, being turned on and off by the microprocessor chip 8031AH. Chip 78L05 provides a low, regulated DC voltage. In the 27C64 PROM resides the program corresponding to the flow chart of FIGS. 18 and 19.

Inasmuch as it is desirable to prevent the mixer from operating, except when a capsule is in place and the door 18 is closed, card switch 43 and door switch 44 are provided which normally prevent the CPU from powering the motor 32, unless door 18 is closed, and thereby closes the switch. The CPU remains on, in any case, once the main AC is switched on. An optical speed sensor 45 senses the rotational speed of shaft 33 of motor 32, and relays a corresponding signal to the CPU.

The operation by coded card is self-evident: as one puts the card into the slot 22, the reading head 26 (see FIGS. 5, 6 and 22) is passed over by track 38, causing the head to send a stream of pulses to the control unit, which interprets them as product name, size, type, time and speed values. Then the user presses START, and the capsule mixer agitates the capsule at the speed called for by the card, and for the time called for thereby.

Card actuation, with coded sets of capsules, totally obviates errors in speed and time settings, as long as the color codes on the cards match the colors of the capsules. For example, on the card illustrated, the icon 36 could show a capsule having a brown body with a gray top, meaning, say, that the magnetic track 26 identifies a "Contour, Regular Set, Double Spill" capsule, as provided to the trade by the assignee of this application.

When the control unit 28 reads the track, then LCD display 14 will show the above-quoted capsule identity, and also a set of factory recommended mixing speeds and times. The user may alter a speed and time, and enter it via the keyboard, should the user wish to modify the time and speed that the card is particularly calling for.

Experienced dentists tend to develop their own preferences for speed and time, which differ from those of capsule manufacturers. Also, it may be that the dentist desires to modify the card-set time and/or speed only slightly. In such case, after the card has been inserted, and before pushing start, the user can respectively press the "SET SPEED" or "SET TIME" control, then either the plus (+) key, or the minus (−) key thereof, in order to "jog" the setting in small increments or decrements, for speed or time, respectively. This feature works with or without using programmed cards.

As it is old in the art to control agitating mechanisms with microprocessor-based controllers (e.g., U.S. Pat. No. 4,531,839, cited above), the details of the microprocessor configuration for the control unit have not been depicted. However, FIGS. 18 and 19 show a preferred flow chart which will enable one of ordinary skill in the microprocessor programming art to program off-the-shelf microprocessors for controlling the present mixing device.

As FIG. 18 shows, upon POWER UP, the controller scans the key board. Although it is not essential, the present flow chart indicates that the program can provide for "SET LANGUAGE REGISTER TO KEY INPUT". In order to invoke one of up to say seven languages, one presses the corresponding one of the keys 1 through 6, while turning on the capsule mixer's power switch in power entry module 42 (FIG. 22), which provides for connecting the mixer to mains AC. The control unit will contain coding for each language, and the foregoing operation will tell the control unit to choose the language which corresponds to the number key pressed, and to display on the LCD display in that language.

Once there is POWER UP, the number keys revert to their numerical function. Preferably, there is a seventh, default language, English, say, which the controller displays in, if the machine is simply turned on when no number key is being pressed.

Next, but optionally, a proprietary message, e.g., "KERR TM AUTOMIX TM", may be shown, and/or a legend identifying the language (French, English, etc.).

The control scans the playback head 26 and the keyboard. At this point, the display will display the message "MANUAL ENTRY" and the default time and speed settings, and the user may set in a time and/or speed from the keyboard, or insert a card, the resulting settings then showing on the display. The user now inspects the display 14, and if all is to his liking, he pushes the START switch, upon which the control unit executes a typical motor speed control routine, all the while timing the running of the motor, as well as sensing its speed and increasing or decreasing motor current in accordance with a conventional motor speed control routine, in order to cause the speed to approach the desired value.

For example, once up to speed, the energization can be decreased, and thereafter caused to change in inverse proportion to deviations from set speed. In this way, the motor maintains substantially the desired speed until the set-in time for agitating the capsule has expired. The control unit when it senses this then turns the motor off.

Figures 7, 8, 9:
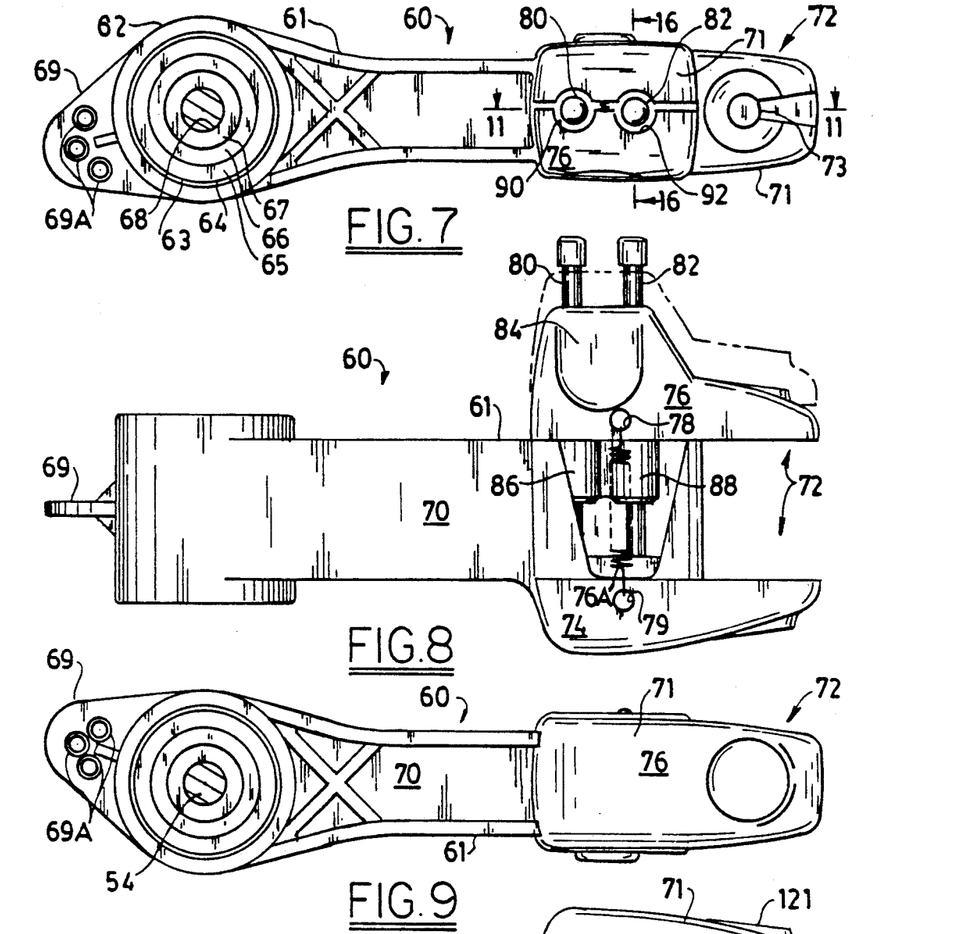
FIG. 7 is a side view of the mixing arm of the device illustrated in FIG. 5.
FIG. 8 is a bottom view of the device of FIG. 7.
FIG. 9 is a side view of the opposite side of the device illustrated in FIG. 7.
Figure 10:
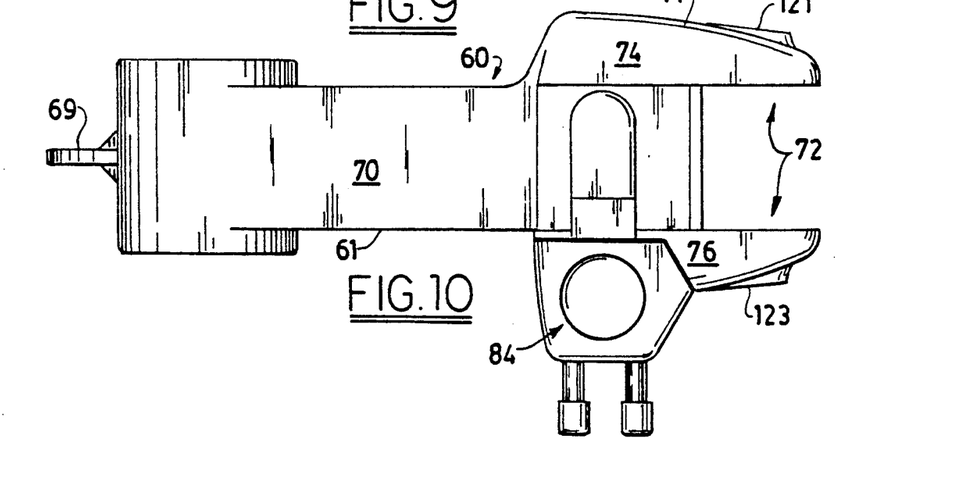
FIG. 10 is a top view of the device illustrated in FIG. 7.
Figure 11:
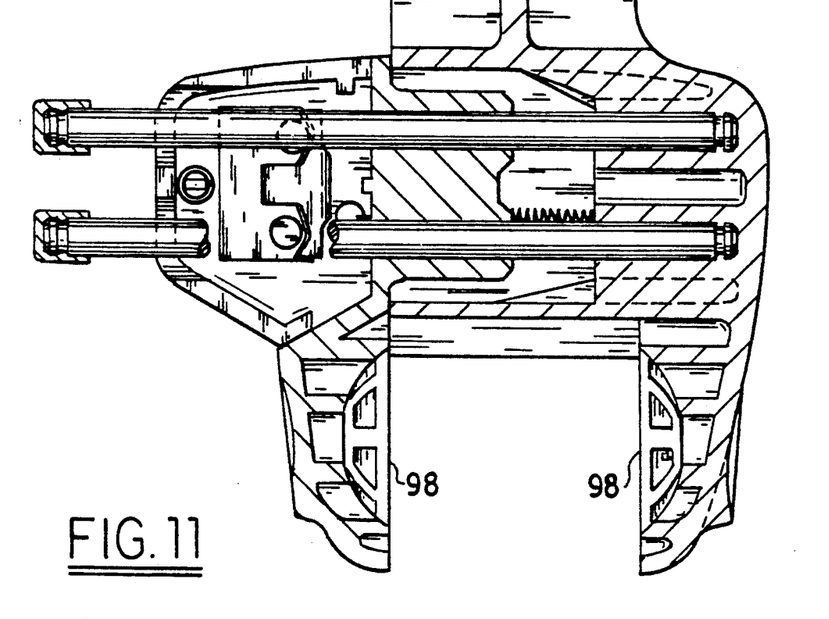
FIG. 11 is an enlarged sectional view of the jaw means of the device of FIG. 8 along line 11—11.
Figure 12:
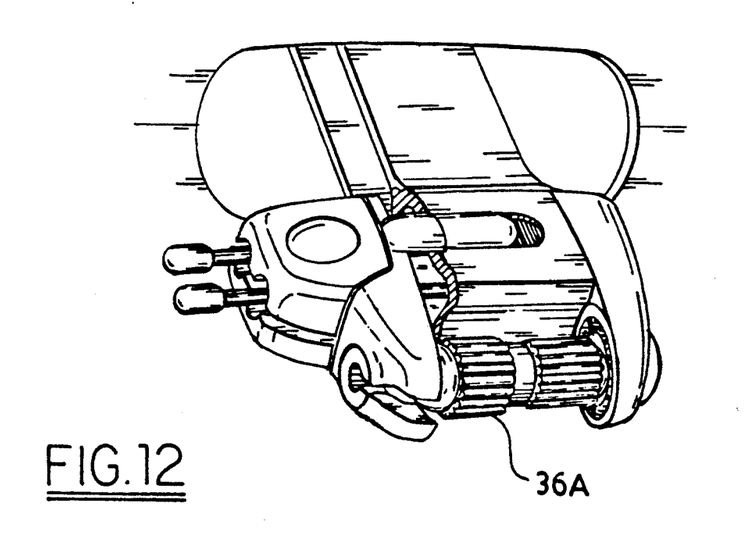
FIG. 12 is a perspective view of the jaw means of the device of FIG. 11.

As shown in FIG. 7, the mixing arm assembly 60 of the present invention comprises a support structure 61, preferably molded out of a plastic material. The support structure 61 at one end contains a cylindrical hub 62 having a cylindrical bore 63. Secured to support structure 61 within bore 63 are a pair of sealed ball bearings 64 (see also FIGS. 5 and 9) having an outer race 65, an inner race 67 and sealed bearings 66. The inner race 67 defines a cylindrical bore 68 designed to receive a rotating cam shaft 54 driven by an appropriate motor 32 (see FIG. 5) when the arm assembly 60 is in the operating position. Each ball bearing 64 is preferably press fit into a seat defined by bore 63, however, ball bearings 64 may be secured to support structure 61 within bore 63 by any convenient means. A plurality of holes 69A are provided in projection 69 extending from cylindrical hub 62 and are designed to receive one end of a fixed spring 55 to be later described. The support structure 61 also includes a central section 70 and distal end 71. The distal end 71 includes a movable jaw assembly 72. Movable jaw assembly 72 includes a pair of metal rods 80 and 82 which are connected to a fixed jaw 74 which is an integral part of distal end 71, with said rods passing through movable jaw 76. The movable jaw 76 slides along rods 80 and 82 and is held in position by spring 76A having one end connected to hole 78 in the side of movable jaw 76 with the other end of spring 76A secured to hole 79 in fixed jaw 74. Spring 76A functions to keep both jaws together in a normally closed position. A pair of rod guides 86 and 88 are molded into moveable jaw 76 each having a hole 87 and allow guides 86 and 88 to slide for controlled movement of jaw 76 along metal rods 80 and 82. The rod guides 86 and 88 also function to hold buttons 106 and 108 in mating engagement to form chamber 109 (see FIGS. 15 and 16). The moveable jaw assembly is slotted at 73 to accommodate dental capsule configurations having projections at one end. The interior gripping portion of both jaws have an inner concave surface 98 (FIGS. 11 and 12) to accommodate the normally rounded ends of typical mixing capsules.

Figure 15:
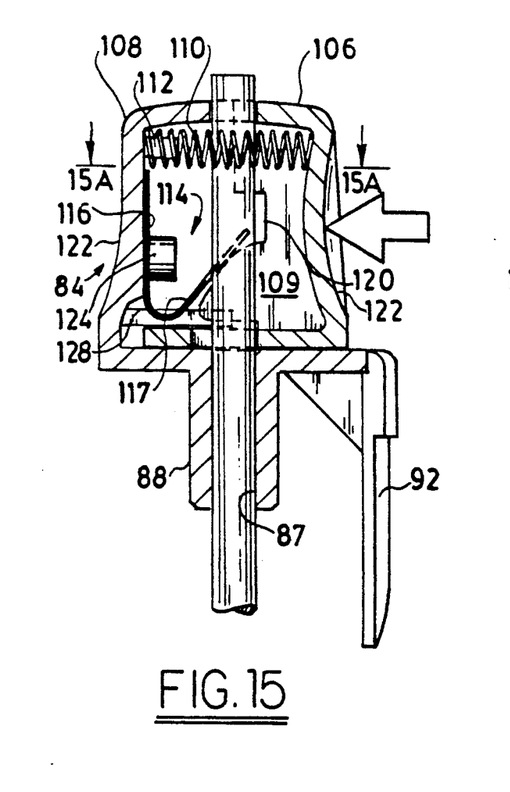
FIG. 15 is a sectional view of the device of FIG. 11 with the brake clip in the unlocked position.
Figure 15A:
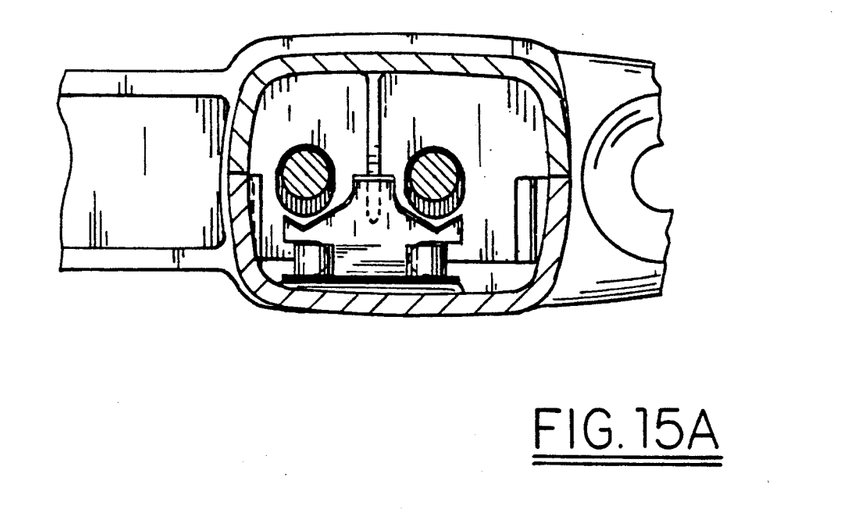
FIG. 15A is a sectional view of the device of FIG. 15 along line 15A—15A.
Figure 16:
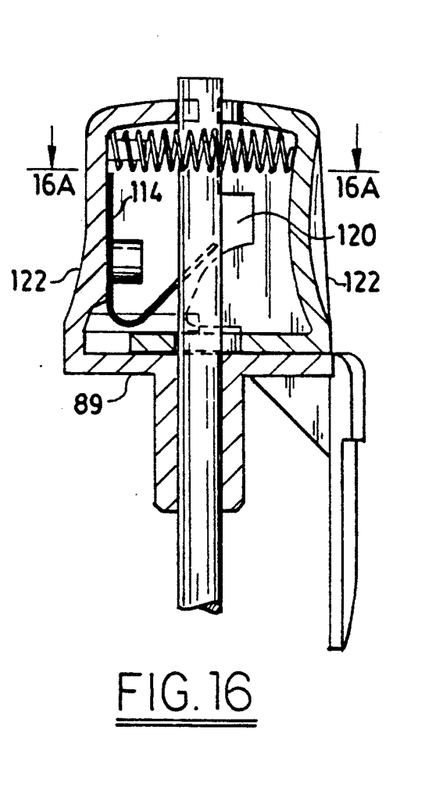
FIG. 16 is a sectional view of the device of FIG. 11 with the brake clip in the locked position.
Figure 16A:
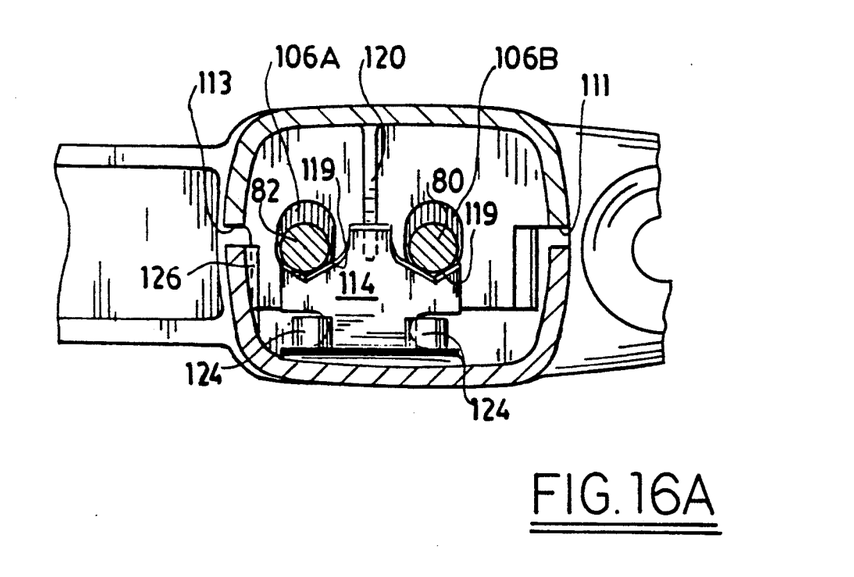
FIG. 16A is a sectional view of the device of FIG. 16 along line 16A—16A.

Moveable jaw assembly 72 further includes a brake assembly 84 which serves to lock the jaw assembly 72 in position during mixing the contents of a dental capsule. The brake assembly 84 forms an integral part of moveable jaw 76 and is designed such that when the mixing arm assembly 60 is in motion, it will maintain the engagement of jaws 74 and 76 on a dental capsule in a locked position. This is an automatic locking feature of the mixing arm assembly 60. The brake assembly 84 comprises a pair of mating release buttons 106 and 108 with button 108 being in a fixed position and release button 106 being movable with respect to release button 108. Release buttons 106 and 108 form the locking chamber 109 through which rods 80 and 82 pass. Holes 87 of collar guides 86 and 88 terminate at wall 89 of button 108. These holes 87 are in alignment with a pair of elongated holes 106A and 106B of button 106. The buttons are also held in sliding engagement through the use of mating projection partition 126 molded in button 108 which engages the complementary left side edge of button 106. The back of button 108 further contains a vertical ridge 128 which engages a complementary slot (not shown) in button 106 for further alignment. Release buttons 106 and 108 have, in the engaged position, holes 90 and 92 (FIG. 7) which permit the rods to pass therethrough and allow button 106 to move toward button 108. A spring 110 is fixed within chamber 109 on post 112 to bias buttons 106 and 108 axially apart at 111 and 113 in the normally locked position as illustrated in FIGS. 16 and 16A. In the particular embodiment illustrated, spring 110 is mounted on post 112 which is molded into release button 108. Brake assembly 84 further includes a metal V-spring clip 114. The V-spring clip 114 is provided within chamber 109 and has one leg 116 held in place on release button 108 by a pair of holes in leg 116 which are mounted on a pair of posts 124 molded into the bottom surface of button 108. Chip 114 further includes a flexible second leg 117 having a pair of terminal edges 119 designed to engage rods 80 and 82 so as to lock the upper jaw 76 in position. By squeezing the release buttons at external concave surfaces 122, release button 106 is moved toward button 108 so as to cause nose section 120, integrally formed with button 106, to flexibly move leg 117 from engagement with rods 80 and 82, thus allowing movable jaw 76 to freely slide on the rods 80 and 82. This unlocked position is illustrated by FIGS. 15 and 15A.

Figure 13:
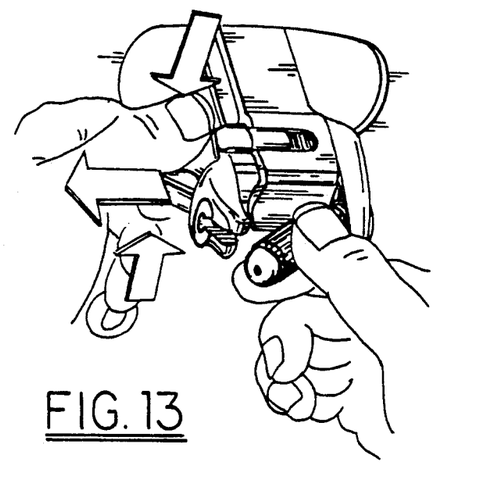
FIG. 13 is a view of the device of FIG. 12 illustrating insertion of a mixing capsule.
Figure 14:
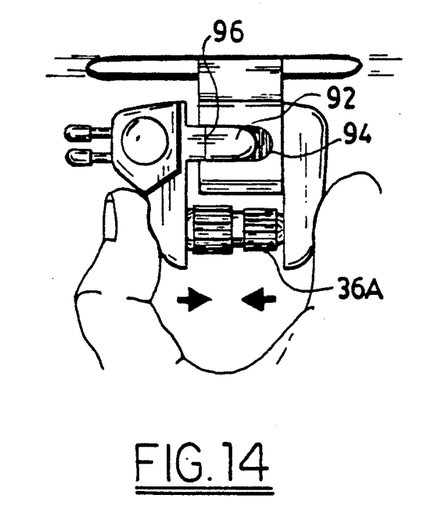
FIG. 14 is a view of the device of FIG. 13 illustrating activation of the capsule.

A dental capsule 36A is loaded into jaw assembly 72 and held in place against concave rounded surfaces 98. To load the capsule the user first squeezes the release buttons 106 and 108 and slides the moveable jaw 76 to the open position as illustrated in FIG. 13. The jaws 74 and 76 have two fingerpads or recessed sections 121 and 123, respectively, on their outside surface which allow for squeezing the jaws closed. With the jaws 72 and 74 in the open position, as illustrated in FIG. 13, a dental capsule 36A is slid into the capsule holder. Moveable jaw 76 is then slid to the right along rods 80 and 82, closing the jaw assembly 72 on to the ends of the capsule with the thumb and forefinger as illustrated in FIG. 14. To activate most capsules, the outer surface 121 and 123 of jaws 74 and 76 are gripped between the thumb and second joint of the index finger and then squeezed hard until the activator indicator guide 92 which travels in groove 94 has lined up with the side of the arm assembly 60. This motion depresses a capsule plunger which fractures an internal diaphragm allowing the contents of the capsule to come in contact with each other. The guide 92 has an alignment line 96 which indicates the relative location of the jaws. In this position the capsule is locked in place with the brake assembly 84 in the locked position. As illustrated in FIGS. 16 and 16A, terminal edges 119 of clip 114 physically in contact with the metal rods 80 and 82, preventing axial movement of the upper jaw 76, thus holding the jaw 76 in the locked position. As illustrated in FIG. 15A, during the loading step, the terminal edges 119 of spring clip 114 are out of contact with the metal rods 80 and 82, allowing the jaw assembly 72 to be opened by sliding moveable jaw 76 along metal rods 80 and 82. In the locked and activated position, the capsule is now ready for mixing of its contents.

An example of mixing capsules suitable for use with the device of the present invention including dental capsules sold by Kerr Manufacturing Company of Romulus, Michigan under the trademarks CONTOUR, TYTIN and SYBRALOY, which are used to mix a silver alloy and mercury to form dental amalgam. A typical capsule device suitable for use with the mixing device of the present invention is shown by U.S. Pat. No. 3,860,114, entitled Multi-Chamber Container which is incorporated herein by reference. These devices are typically actuated by pressing a plunger which ruptures an internal diaphragm which allows two or more components, such as a silver alloy and mercury, to come into contact with each other for mixing by agitation or shaking to form an amalgam.

In operation, the mixing arm assembly 60 is mounted on cam shaft 54 through bore 68 of sealed ball bearings 66 which are separated by spacer 58. The arm assembly 60 is fixed in position by nut 57 at the end of threaded shaft 54 of cam assembly 50 which is connected at its opposite end through a bore 51 which receives drive shaft 33 of motor 32. The drive shaft 33 is held in place by a set screw 52 on the barrel portion 53 of the cam assembly 50. The bore 68 in bearings 64 allows for rotation of the cam shaft 54. In one embodiment, cam shaft 54 is mounted 6 ¼ degrees off axis with respect to the axis of motor shaft 33. The arrows at the end of shaft 54 in FIG. 5 illustrate the off-axis concept. As illustrated in FIG. 5, this apparatus is set up to produce to the desired configuration and motion for mixing the contents of the dental capsule. In the embodiment shown, a flat figure "8" motion is produced due to the arm being held in place by spring 55 attached to motor bracket 56 and the off-axis cam assembly 50. In one embodiment, the path amplitude of the arm is approximately 0.74 inches (18.8 mm) with the off-axis cam being used to produce a flat figure "8" motion. The arrows at the end of the jaw assembly indicate the amplitude of the mixing motion. A typical cycle for mixing a given dental capsule is 10 seconds at a speed of 3600 rpm. A suitable range for the motor speed and mixing time is from 3,000 to 4,200 rpm motor shaft speed for a time of from about 5 to 12 seconds.

Any suitable electric motor may be used with the mixing device of the present invention. An example of a suitable motor is a 90 volt, 1/15 hp DC series wound electric motor having a maximum speed 10,000 rpm.

It should be further understood that the device of the present invention may also be used to mix any suitable materials other than dental. While the invention has been described in detail with respect to specific embodiments thereof, it will be understood by those skilled in the art that variations and modifications may be made without departing from the essential features thereof.

What is claimed is:

1. A dental mixing machine in which mixing speed and time are controlled by stored data system, the machine comprising a motor, a mechanism for receiving a dental capsule to be agitated, and control means, the motor being controlled by the control means to cause the mechanism to agitate a dental capsule received therein, wherein the control means is responsive to specific agitation parameters for the dental capsule, the machine having entry means for receiving a card having a record of the specific agitation parameters, the entry means being connected to the control means for entering the agitation parameters into the control means thus controlling mixing based on the record.

2. A machine according to claim 1, in which the card is magnetically coded with the agitation parameters.

3. A machine according to claim 2, in which the parameters include speed of mixing and time of mixing.

4. A machine according to claim 1, in which the card also has thereon a visual display of information relating to the agitation parameters.

5. A machine according to to claim 4, in which the visual display comprises a representation of a capsule to which the agitation parameters relate.

6. A machine according to claim 5, in which the representation and the capsule are color-coded.

7. A machine according to claim 5, having display means connected to the control means for displaying information from the data system.

8. A machine according to claim 7, having keyboard means constructed and arranged for entry of agitation parameters, and the display means being responsive to the keyboard means to display the last-entered parameters.

9. A dental capsule mixing machine in which mixing speed and time are controlled by a stored data system, said machine comprising in combination, a motor, a mechanism for receiving a dental capsule to be agitated, and control means, and wherein said motor is controlled by said control means for causing said mechanism to agitate said dental capsule, the improvement comprising an arrangement wherein said control means is responsive to specific agitation parameters which differ depending on the nature of the material in said dental capsule and its end-use, said machine having entry means constructed and arranged for receiving a card having a record of said specific agitation parameters, said entry means being connected to said control means, for entering said agitation parameters contained on said card.

10. A method for mixing a dental capsule, in which mixing speed and time are controlled by a stored data system which comprises the steps of:
 (a) providing a dental mixing machine having a motor, a mechanism for receiving a dental capsule to be agitated, and control means, the motor being controlled by the control means to cause the mechanism to agitate a dental capsule received therein wherein the control means is responsive to specific agitation parameters for the dental capsule, the machine having entry means for receiving a card having a record of the specific agitation parameters, with the entry means being connected to the control means for entering the agitation parameters into the control means thus controlling mixing based on the record;
 (b) selecting a dental capsule to be agitated and a card corresponding thereto;
 (c) placing the dental capsule in the receiving means;
 (d) placing the card in the entry means; and
 (e) activating said motor to cause the mixing machine to agitate the dental capsule at a mixing speed and time, in accordance with the predetermined agitation parameters.

11. A method according to claim 10, in which the agitation parameters recorded on the card are varied by the user prior to operation of the machine.

12. The method of claim 10 in which the card and the capsule both carry visual information matching the card to the capsule.

13. A method according to claim 12, in which the visual information on the card comprises a representation of the capsule.

* * * * *